United States Patent
Barnes, Jr. et al.

(10) Patent No.: US 6,453,900 B1
(45) Date of Patent: Sep. 24, 2002

(54) INHALER DEVICE

(75) Inventors: William M. Barnes, Jr., Walnutport; Dennis Little, Allentown; David D. McClanahan, Harleysville; James B. Eldon, III, Barto, all of PA (US)

(73) Assignee: Pulmonary Services, Inc., PA (US)

( * ) Notice: Subject to any disclaimer, the term of this patent is extended or adjusted under 35 U.S.C. 154(b) by 232 days.

(21) Appl. No.: 09/591,610

(22) Filed: Jun. 9, 2000

(51) Int. Cl.$^7$ ............................................. A61M 16/00
(52) U.S. Cl. ........................... 128/200.23; 128/200.14; 128/203.12; 239/338
(58) Field of Search ..................... 128/200.14, 200.18, 128/200.21, 200.22, 200.23, 203.12; 222/162, 165, 402.1, 402.13, 402.15; 239/338

(56) References Cited

U.S. PATENT DOCUMENTS

| | | | |
|---|---|---|---|
| 3,344,959 A | * 10/1967 | Faso | 222/162 |
| 3,405,843 A | * 10/1968 | Watson, Jr. | 137/846 |
| 3,456,644 A | 7/1969 | Thiel | |
| 3,490,452 A | * 1/1970 | Greenfield | 128/200.23 |
| 3,789,843 A | 2/1974 | Armstrong et al. | |
| 3,826,413 A | 7/1974 | Warren | |
| 4,470,412 A | * 9/1984 | Nowacki et al. | 128/200.18 |
| 4,592,348 A | * 6/1986 | Waters, IV et al. | 128/200.23 |
| 4,648,393 A | * 3/1987 | Landis et al. | 128/200.23 |
| 4,664,107 A | * 5/1987 | Wass | 128/200.23 |
| 4,678,106 A | 7/1987 | Newell et al. | |
| 4,765,515 A | * 8/1988 | Lippman | 222/162 |
| 4,796,614 A | * 1/1989 | Nowacki et al. | 128/200.14 |
| 4,834,083 A | 5/1989 | Byram et al. | |
| 4,926,852 A | 5/1990 | Zoltan et al. | |
| 5,007,419 A | 4/1991 | Weinstein et al. | |
| 5,027,806 A | * 7/1991 | Zoltan et al. | 128/200.23 |
| 5,119,806 A | * 6/1992 | Palson et al. | 128/200.14 |
| 5,203,323 A | 4/1993 | Trittle | |
| 5,217,004 A | * 6/1993 | Blasnik et al. | 128/200.14 |
| 5,318,016 A | 6/1994 | Mecikalski | |
| 5,347,998 A | * 9/1994 | Hodson et al. | 128/200.23 |
| 5,355,873 A | * 10/1994 | Del Bon et al. | 128/200.23 |
| 5,377,869 A | * 1/1995 | Weiss et al. | 222/1 |
| 5,447,150 A | * 9/1995 | Bacon | 128/200.14 |
| 5,474,058 A | 12/1995 | Lix | |
| 5,497,765 A | * 3/1996 | Praud et al. | 128/200.23 |
| 5,511,540 A | 4/1996 | Bryant et al. | |
| 5,623,920 A | * 4/1997 | Bryant | 128/200.14 |
| 5,724,986 A | * 3/1998 | Jones et al. | 128/200.14 |
| 5,738,087 A | * 4/1998 | King | 128/200.23 |
| 5,746,197 A | 5/1998 | Williams | |
| 5,809,996 A | 9/1998 | Alldredge | |
| 5,957,125 A | 9/1999 | Sagstetter et al. | |
| 6,062,214 A | * 5/2000 | Howlett | 128/200.14 |
| 6,109,261 A | * 8/2000 | Clarke et al. | 128/200.23 |

* cited by examiner

Primary Examiner—Aaron J. Lewis
Assistant Examiner—Mital Patel
(74) Attorney, Agent, or Firm—Schnader Harrison; Segal & Lewis LLP

(57) ABSTRACT

An inhaler for releasing an aerosol from a container having a lip and an outlet normally sealed by a stem movable relative to the lip. The inhaler has an elongate body comprising a chamber having a first end and a second end, the chamber forming an opening at the first end of the chamber. The elongate body further comprises a stem block with a socket adapted to receive the stem of the container, a dispensing nozzle and a flow restrictive valve. The dispensing nozzle is adjacent to the stem block for providing communication between the socket and the chamber and is adapted to direct a discharge of the aerosol from the container stem into the chamber. The flow restrictive valve is in open communication with the chamber and responsive to a change in fluid pressure. The inhaler also has an actuator pivotably attached to the elongate body. The actuator has an opening adapted to receive the lip of the container and a detent for forming a removable connection between the lip and the actuator. The actuator opening is located substantially directly above the socket.

27 Claims, 10 Drawing Sheets

INHALER DEVICE

FIELD OF THE INVENTION

This invention relates to an inhaler for dispensing an aerosol from a container. In particular, the invention relates to an inhaler for dispensing medication from a metered dose canister with minimal effort and convenience to the user, and while preventing undesired rates of inhalation of the dispensed medication.

DESCRIPTION OF THE RELATED ART

Inhalers are commonly used to dispense an aerosol for treatment, or alleviation of the effects of respiratory complaints, such as asthma. One of the most convenient choices of treatment of respiratory complaints has been the inhalation of medicament from a drug solution or suspension in a metered dosed pressurized inhaler (MDI).

Standard metered dosage inhalers have effectively produced an aerosol of medication in a predetermined dosage for delivery to the lungs. However, awkward dispensing mechanisms as well as inefficient delivery systems decrease the likelihood that the medication effectively reaches the users lungs. Known inhalation devices typically comprise a tubular housing or sleeve in which a pressurized aerosol container is located and a mouthpiece or nozzle leading out of the tubular housing. In use, the aerosol container is placed into the housing, which is then held by the patient in a more or less upright position, and the mouthpiece or nozzle of the inhalation device is placed in the mouth or nostril of the patient. The patient inhales through either the mouthpiece or nozzle while simultaneously releasing the medication from the aerosol container. With all such devices, the patient releases the medication either manually by pressing on a bottom surface of the aerosol container, or using an actuator that exerts a force on the bottom surface of the aerosol container.

The most significant problem associated with such inhalation devices has been the difficulty for many patients to coordinate the manual release of the medication with the initiation of inspiratory effort. Indeed, many people not afflicted with asthma, bronchitis, emphysema, or other respiratory difficulties have demonstrated that they are unable to coordinate these tasks properly. Patients suffering from the distress of broncho-constriction have much greater difficulty. Patients such as children, geriatrics, arthritics, the physically challenged and the infirm also have great difficulty in holding the inhalation device to the mouth or nostril while depressing the aerosol container. As a result, a large percentage of inhaler users may fail to inhale the proper dosage of medicament. Thus, there are many groups of patients who could receive an increased benefit from aerosol medicaments if an inhaler were available that minimized the problem of coordinating the release of the medicament with inhalation.

As mentioned above, some prior art inhalers incorporate an actuator that exerts a force on the bottom surface of the container to assist the release of the medication. Examples of these inhalers are found in U.S. Pat. No. 4,678,106 to Newell, and U.S. Pat. No. 4,834,083 to Byram. In these prior art inhalers, the shape of the inhaler is dependent upon the length of the container. This is problematic in that it prohibits patients from using one inhaler regardless of the length or manufacturer of the canister. Thus, patients who take more than one medication would need a number of different sized inhalers designed to fit each specific canister.

Another known problem with prior art inhalers is the difficulty in achieving optimal deposition of medication. Prior art metered dose inhalers, upon actuation, dispense short bursts of medication traveling at a relatively high discharge velocity. However, it is known in the art that a slow and deep inhalation coordinated with activation of the inhaler increases the amount of medication received in the lungs. Much of the prior art has attempted to solve this problem by providing various enlarged chambers that receive the discharge from the inhaler and hold it therein until withdrawn by the user. The ACE® aerosol cloud enhancer, U.S. Pat. No. 4,926,852 issued to Zoltan, et al., U.S. Pat. No. 5,203,323 issued to Tritle, U.S. Pat. No. 5,042,467 issued to Foley and U.S. Pat. No. 4,470,412 issued to Nowacki, et al. are each examples of expansion chambers. However, providing a chamber alone does not avoid ineffective inhalation.

Some of these prior art inhalers, such as the ACE® aerosol cloud enhancer, have included a coaching whistle at the end of the chamber that sounds if a patient inhales above a desired inhalation rate. However, patients who cannot hear the whistle or choose to ignore the whistle will suffer from ineffective administration of the medication. Furthermore, the coaching whistle has an unobstructed opening through which the medication can quickly and easily escape from the chamber either by exhalation of the patient or by the natural flow of the medication.

A need exists for an inhaler that requires minimal strength to administer medication, that is capable of administering medications in containers of a variety of volumes, and capable of containing the medication in the chamber while prohibiting rapid inhalation. The present invention addresses these needs by providing an inhaler with a unique activation system to reduce the effort associated with the delivery of inhaled medication from a variety of containers, and a flow restrictive valve to regulate the rate of inhalation of the medication, thereby maintaining a therapeutic inspiratory flow.

SUMMARY OF THE INVENTION

The invention relates to an inhaler for releasing an aerosol from a container. The container has a lip and an outlet normally sealed by a stem. The stem is movable relative to the lip. The inhaler has an elongate body, and an actuator pivotably attached to the elongate body. The elongate body has a chamber, a stem block, a dispensing nozzle and a flow restrictive valve. The chamber has an opening at one end and, in a preferred embodiment, the opening is adapted to receive a mouthpiece or a mask attachment. The stem block has a socket adapted to receive the container stem. The dispensing nozzle is adjacent to the stem block and provides communication between the socket and the chamber. The dispensing nozzle is also adapted to direct a discharge of the aerosol, when actuated, from the container stem into the chamber. The flow restrictive valve is in open communication with the chamber and responsive to a change in fluid pressure, typically resulting from inhalation and exhalation of the user of the inhaler. The actuator is pivotably attached to the elongate body and has an opening adapted to receive the lip of the container. The actuator also has a detent for forming a removable connection between the lip of the container and the actuator. The actuator opening is located substantially directly above the socket.

In a preferred embodiment, the chamber has a door pivotably attached to the chamber. The door provides access to the inside of the chamber to store the canister and mouthpiece. In another embodiment, the dispensing nozzle is adapted to direct a discharge of the aerosol toward the opening of the chamber. The dispensing nozzle shape, preferably is a tee-bar shape, an oval, conical or cylindrical. In one embodiment, the chamber is elliptically shaped and the dispensing nozzle is further adapted to shape the discharge of the aerosol into a flattened plume.

The flow restrictive valve may comprise a leaf valve, a flexible member, or a movable cylinder. The flow restrictive valve is responsive to a change in fluid pressure. The flow restriction valve assists in controlling the flow of fluid and has components that are moveable from a substantially open position to a substantially closed position at about predetermined maximum inhaled flow rate. A leaf valve stop may be incorporated into the flow restrictive valve to prohibit the leaf valve, flexible member, or moveable cylinder from closing at the predetermined maximum inhaled flow rate. In one embodiment, if the user exhales into the chamber, the valve will substantially close and cause a redirection of fluid through a fluid relief hole in the mouthpiece wall.

BRIEF DESCRIPTION OF THE DRAWING

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

While the invention will be described in connection with one or more preferred embodiments, it will understood that the description is not intended to limit the invention to the described embodiments. On the contrary, the description is intended to cover all alternatives, modifications and equivalents as may be included within the spirit and scope of the invention as defined by the appended claims.

Figure 1:
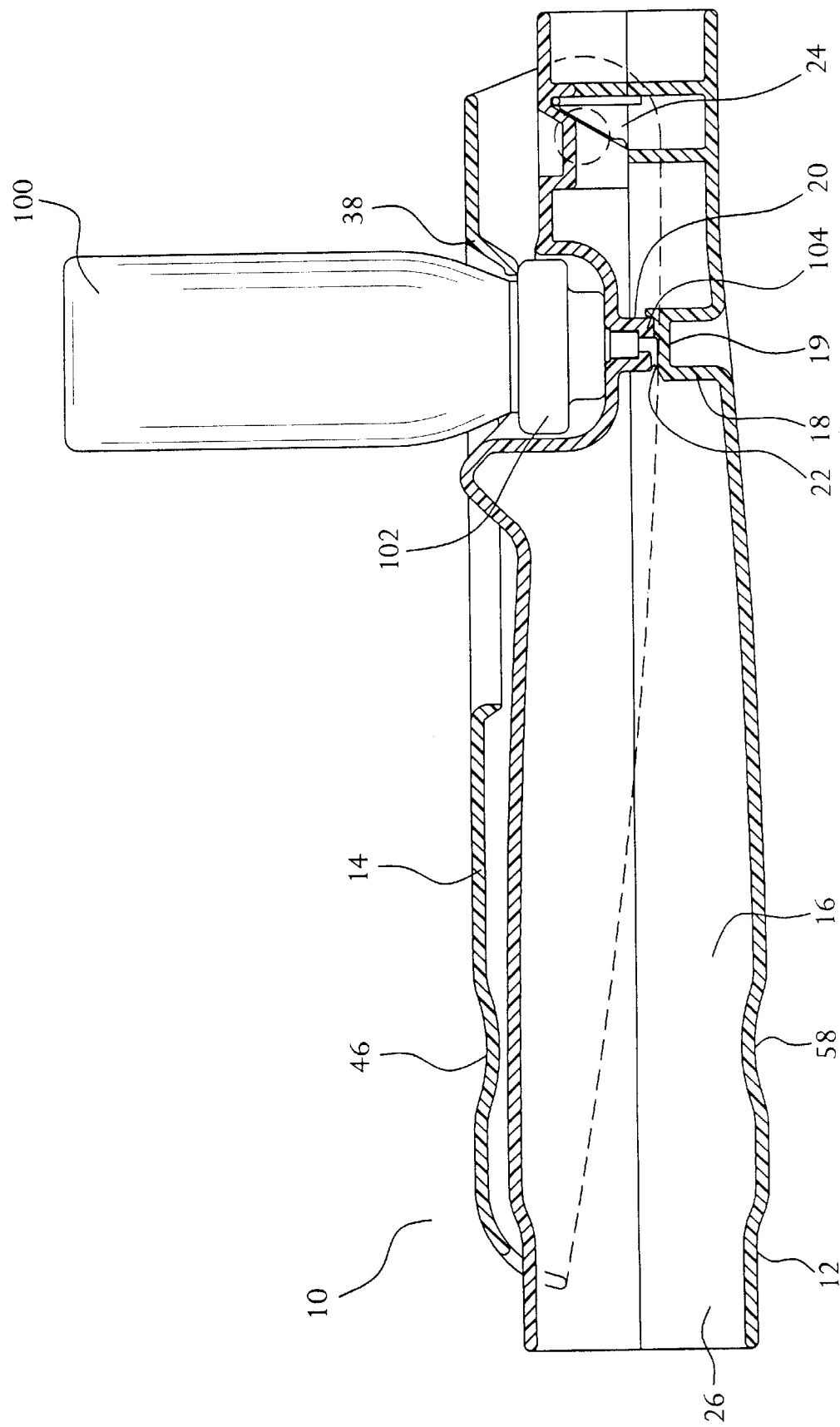
FIG. 1 illustrates a side cross-sectional view of a preferred form of an inhaler device according to the invention, shown with the inhaler engaging a pressurized canister.

Referring now to the drawings, wherein like numerals indicate like elements, there is shown in FIG. 1 an inhaler 10 according to an embodiment of the invention. The inhaler 10 comprises an elongate body 12 and an actuator 14 pivotably attached to the elongate body 12. The inhaler 10 is adapted to receive an aerosol from a container to enable a user to dispense the aerosol and inhale the aerosol effectively and with minimal effort. The container contemplated for use with the invention preferably comprises a lip and an outlet sealed by a stem movable relative to the lip. More preferably, and as depicted in FIG. 1, the container is a pressurized canister 100 having lip 102 and stem 104. According to an embodiment of the invention, the inhaler 10 can accommodate a variety of pressurized canisters of varying lengths, including canisters ranging in length from 1.434 inches to 2.614 inches. A sample of manufacturers of pressurized canisters include Rhone-Poulenc Rorer Pharmaceuticals Inc., Fort Washington, Pa., Dey Laboratories, Napa Valley, Calif., Allen & Hanburys (Division of Glaxo-Wellcome), Research Triangle Park, North Carolina, Warrick Pharmaceuticals Co., Niles, Ill. Graham-Field, Inc., Bay Shore, N.Y., Fisons of Bangladesh, India and Astra Zeneca of Wilmington, Del.

Although the container has been described, in particular, as a pressurized canister 100, it is to be understood that any container or attachment comprising a lip and a stem are contemplated by this invention.

Figure 2:
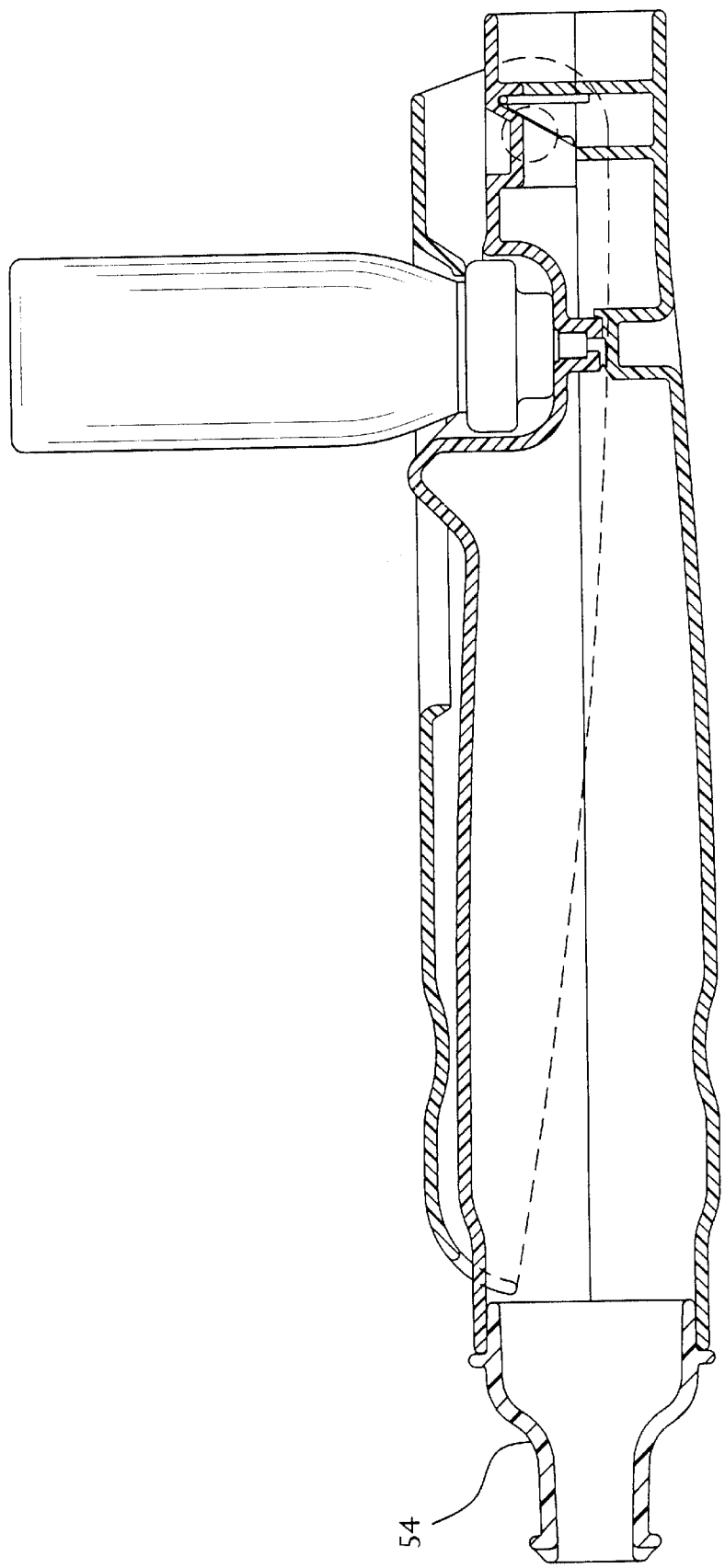
FIG. 2 shows an embodiment of the invention wherein the inhaler depicted in FIG. 1 is adapted to receive a mouthpiece.
Figure 3:
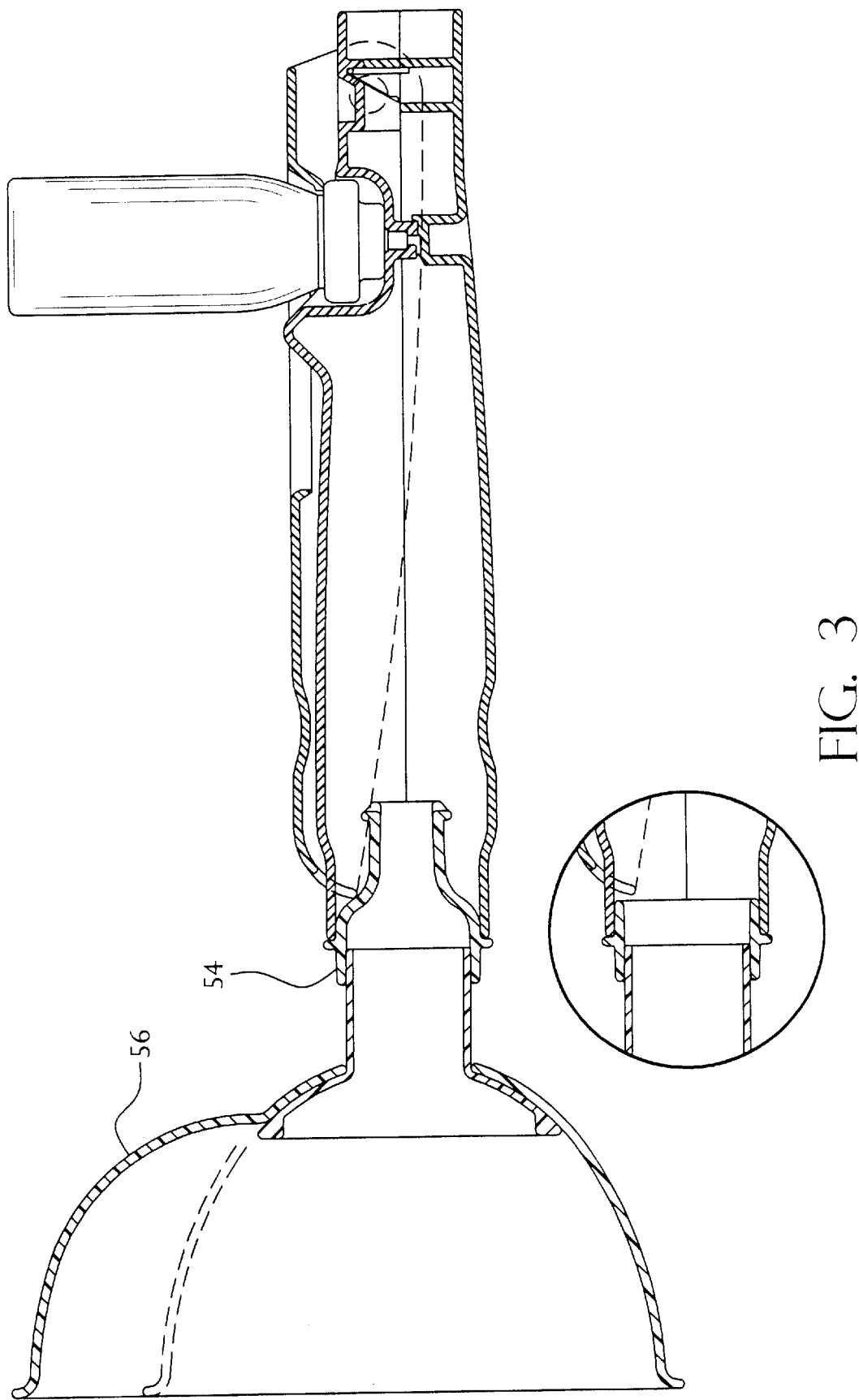
FIG. 3 shows an embodiment of the invention wherein the inhaler depicted in FIG. 1 is adapted to receive a mask attachment.
Figure 12:
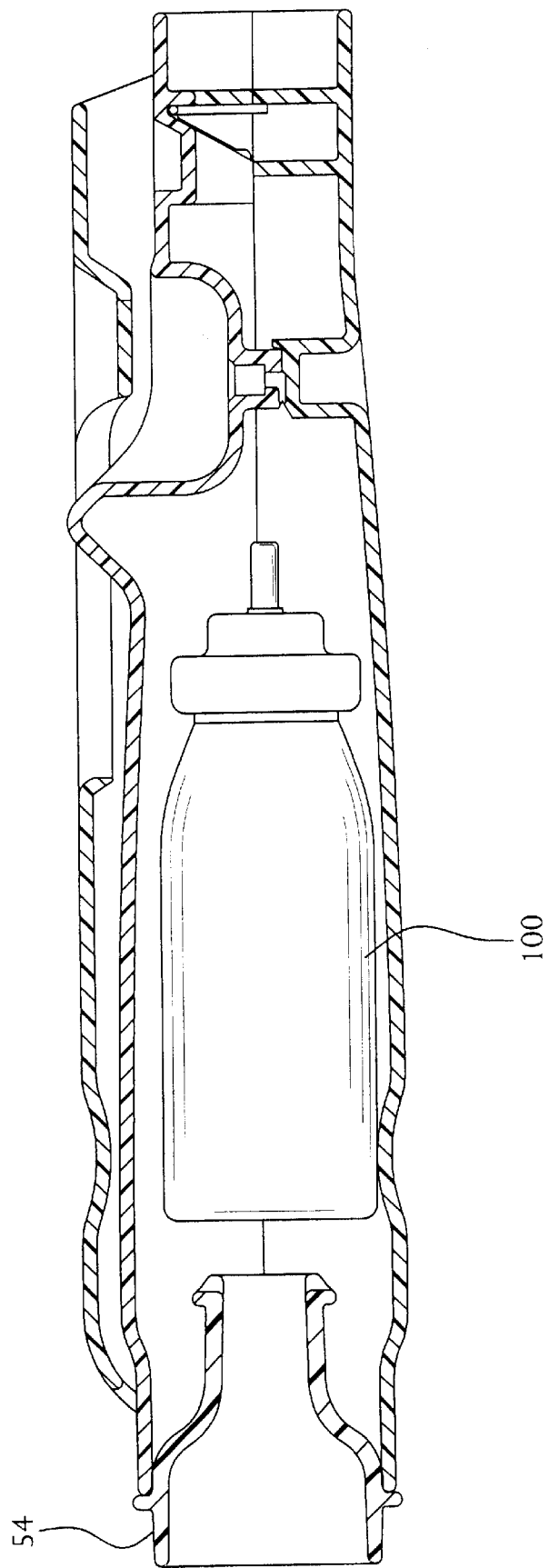
FIG. 12 shows the embodiment of FIG. 2 with the canister and mouthpiece stored in the chamber.

The elongate body 12 of inhaler 10 has a chamber 16, a stem block 18 with a socket 20, a dispensing nozzle 22 and a flow restrictive valve 24. The chamber 16 has an opening 26 to facilitate inhalation of the aerosol by the user. The chamber opening 26 may be adapted to receive a mouthpiece 54, as shown in FIG. 2, or a mask attachment 56, as shown in FIG. 3. In the embodiment of FIG. 3, the mouthpiece 54 is used in conjunction with the mask attachment 56. Preferably, the chamber 16 is of sufficient volume and shape to store the canister 100, the mouthpiece 54 or both, as shown in FIG. 12. The embodiment depicted in FIG. 1 shows an elliptically-shaped chamber 16, however, the invention contemplates a variety of shapes and volumes of the chamber 16. The chamber 16, preferably, has a volume in the range of about 120 cubic centimeters to about 150 cubic centimeters.

The stem block 18, socket 20, and dispensing nozzle 22 of the elongate body 12 facilitate the dispensation of the aerosol from the pressurized canister 100. The stem block 18 forms the socket 20. The socket 20 is adapted to receive the stem 104 of the canister 100. A portion of the stem block 18 provides a stop 19 for the stem 104 when the stem 104 is inserted into the socket 20. The dispensing nozzle 22 is adjacent to the stem block 18 and provides communication between the socket 20 and the chamber 16. The dispensing nozzle 22 is adapted to direct a discharge of aerosol from the stem 104 into the chamber 16. Preferably, the discharge of the aerosol is directed toward the opening 26 of the chamber 16. The shape of the dispensing nozzle 22 affects the spray pattern of the aerosol into the chamber 16. An embodiment of the invention contemplates a dispensing nozzle 22 capable of creating a fan-shaped spray pattern of the aerosol with a spray angle substantially in the range of 15 to 90 degrees, such as the BEX F Series Flat "V" spray nozzle sold by BEX Spray Nozzle of Livonia, Mich. In one embodiment, the dispensing nozzle 22 is selected to discharge the aerosol into the chamber 16 in the shape of a flattened plume. The dispensing nozzle 22 may be a variety of different shapes, including a tee-bar, oval, conical and circular. Preferably, the dispensing nozzle 22 is molded together with the elongate body 12.

Figure 4:
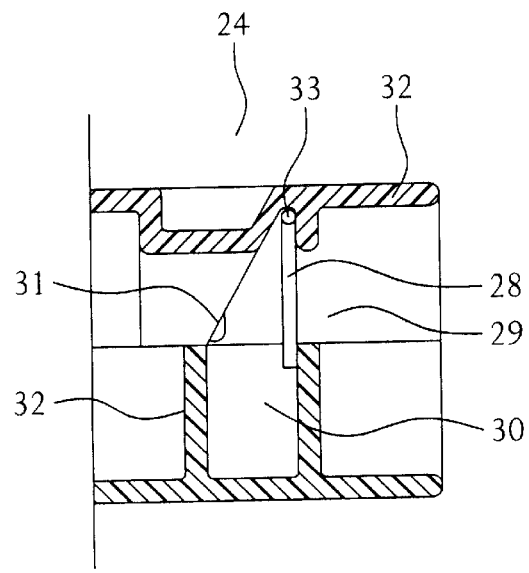
FIG. 4 is a sectional view of a flow restrictive valve according to the embodiment depicted in FIG. 1, showing the valve in a closed position to prevent back pressure.

FIG. 4 shows the flow restrictive valve 24 of FIG. 1 in greater detail. The flow restrictive valve 24 of the elongate body 12 has a leaf valve 28 movable within a bore 30. A valve base 32 forms the bore 30 and also forms an port 29. Preferably, the leaf valve 28 is pivotably attached to valve base 32 at a point 33. The leaf valve 28 may be of any geometric shape and is shown in FIG. 4 as a flat rectangular disk. The bore 30 may be of any shape sufficient to allow movement of the leaf valve 28 within the bore 30. A leaf valve stop 31 is included in valve base 32. Although FIG. 1 and 4 show a leaf valve 24 in an embodiment of the invention, the invention contemplates other structures that substantially produce the same results as the leaf valve 28, such as a flexible member 35 (shown in FIG. 7), a moveable cylinder valve, and a diaphragm valve.

In operation, the leaf valve 28 is normally in the closed position, as shown in FIG. 4, to prevent the contents of the chamber 16 from leaking into the atmosphere through the port 29. If a user of the inhaler 10 inadvertently exhales into the chamber 16, thereby creating back pressure, the leaf valve 28 responds by remaining closed and prohibiting the contents of the chamber 16 from leaking into the atmosphere through the port 29.

Figure 6:
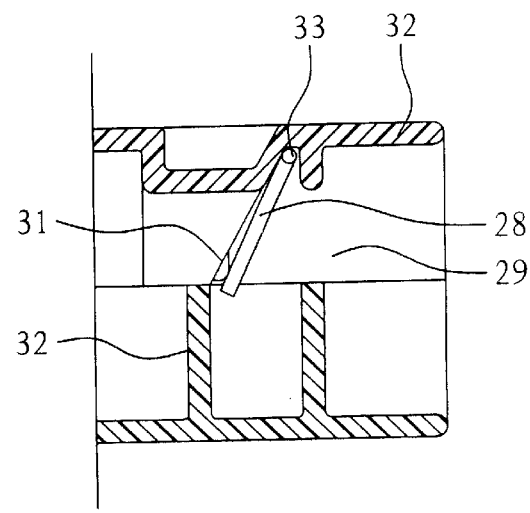
FIG. 6 is a side view of the flow restrictive valve of FIG. 4 shown in a substantially closed position due to over-inhalation.
Figure 5:
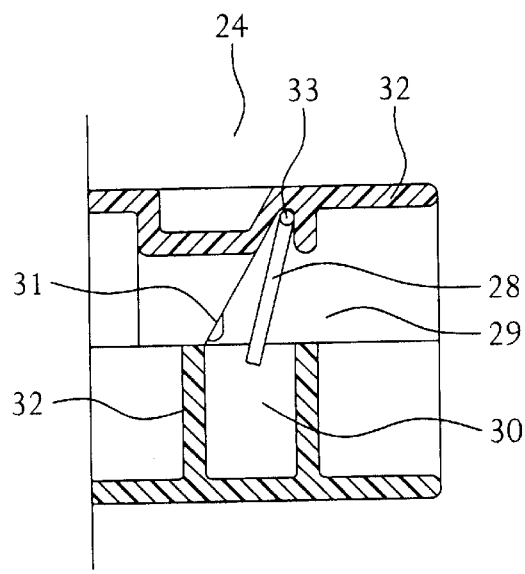
FIG. 5 is a side view of the flow restrictive valve of FIG. 4 shown in a substantially open position under optimal inhalation rate conditions.

When a user inhales, the flow restrictive valve 24 opens allowing air through the port 29. The flow restrictive valve 24 responds up to a predetermined maximum inhaled flow rate, at which point the valve 24 moved from a substantially open position, as shown in the embodiment in FIG. 5, to a substantially closed position as shown in the embodiment of FIG. 6. As shown in FIGS. 4–6, the leaf valve stop 31 prevents the leaf valve 28 from completely closing in an over-inhalation condition.

Figure 7:
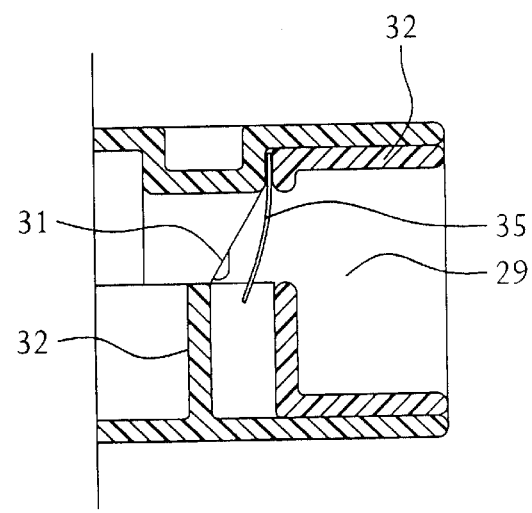
FIG. 7 shows an alternative embodiment of a flow restrictive valve according to an aspect of the invention.

FIG. 7 shows an embodiment of the invention wherein the flow restrictive valve 24 comprises a flexible member 35 affixed to the valve base 32. The flexible member 35 flexes in response to inhalation and exhalation to produce results similar to the results produced by the pivotably attached leaf valve described above.

In a preferred embodiment, the predetermined maximum inhaled flow rate is controlled by a tension switch (not shown). The flow rate is preferably in the range of about 1 to about 100 liters per minute. In another embodiment, the flow rate is less than about 80 liters per minute. Most preferably, the flow rate is less than substantially about 35 liters per minute. In operation, the flow restrictive valve 24 substantially prohibits inhalation of the aerosol at or about the predetermined maximum flow rate.

Preferably, chamber 16, dispensing nozzle 22 and stem block 18 are molded as a single piece, or unibody, by known methods such as blow molding or injection molding. More preferably, the valve base 32 is also molded with chamber 16, dispensing nozzle 22 and stem block 18.

Figure 8:
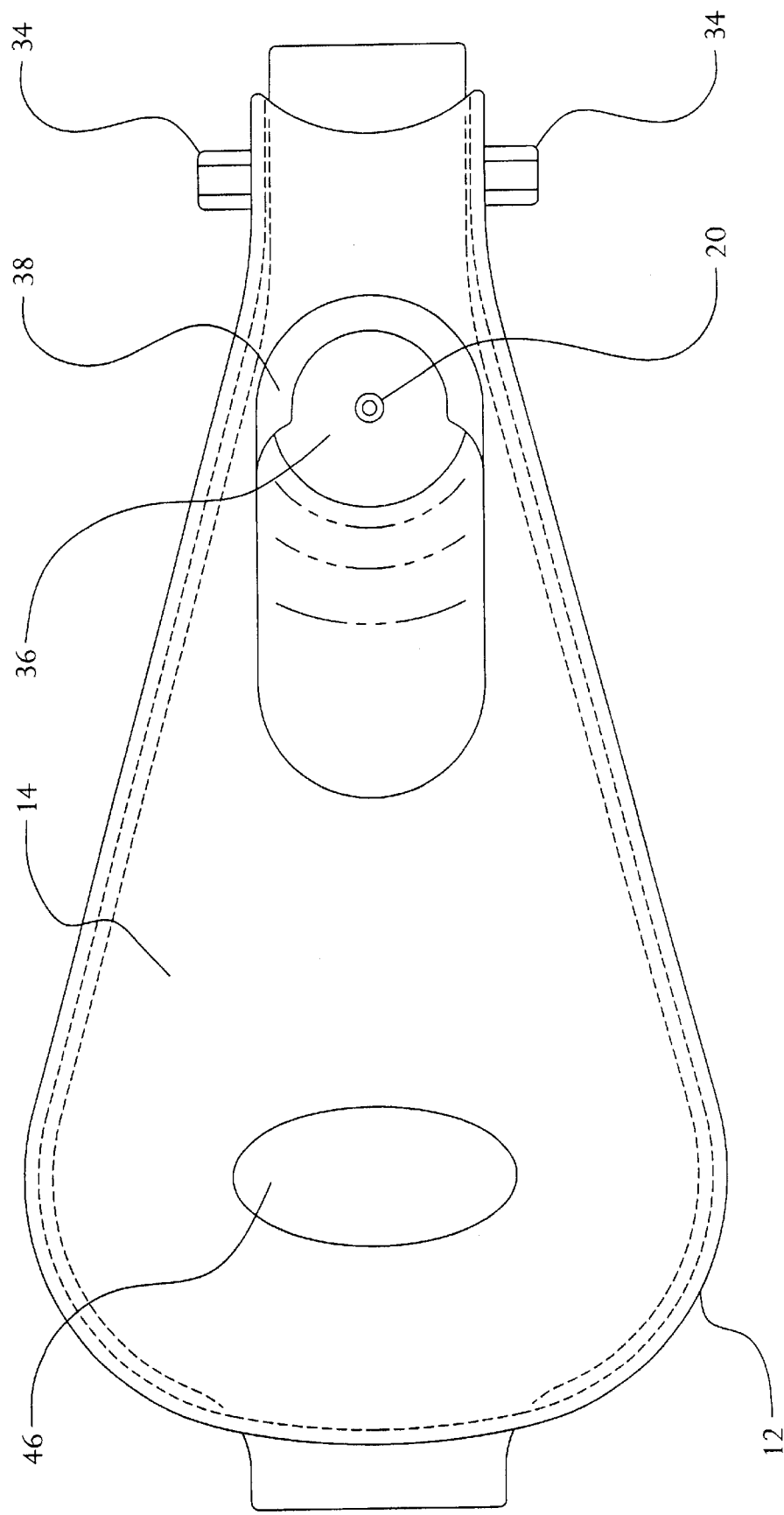
FIG. 8 is a top view of the actuator depicted in FIG. 1.
Figure 11:
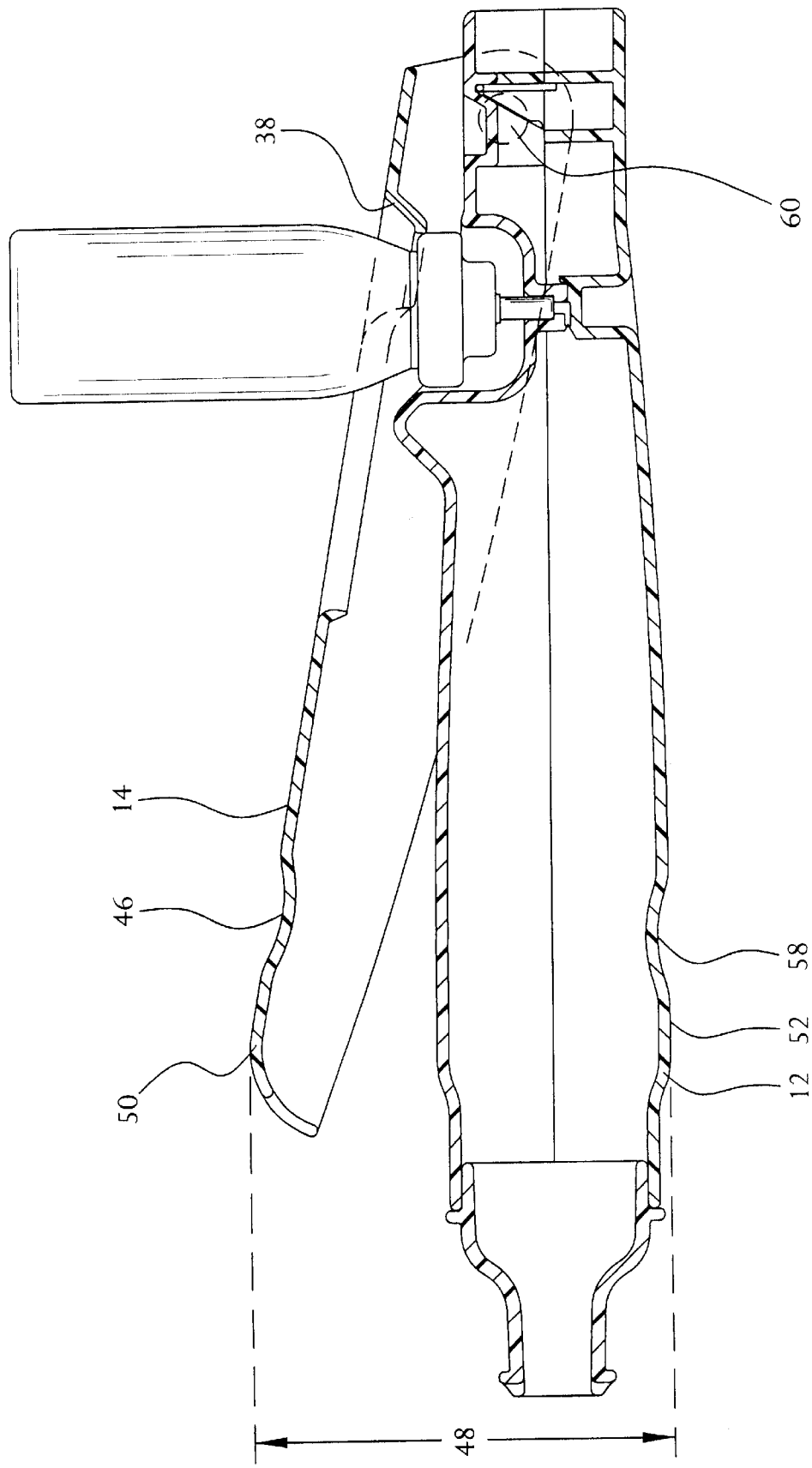
FIG. 11 shows the embodiment of FIG. 1 with the actuator in a non-actuated position.

Referring to FIGS. 8, 11 and back to FIG. 1, there is shown an actuator 14 of the inhaler 10. The elongate body 12 includes at least one shaft 34, and preferably, a pair of opposing shafts as shown in FIG. 8. The actuator 14 includes portions defining at least one hole 60 for receiving the shaft 34. Each shaft 34 and hole 60 forms a pivotal connection between the actuator 14 and the elongate body 12. Although the shaft 34 and hole 60 combination is exemplary and shown in FIGS. 1, 8, and 11, the invention contemplates all known methods of pivotable attachment, such as, for example, a hinged connection.

In the embodiment shown in FIG. 1, the actuator 14 is substantially parallel to the elongate body 12 when the actuator 14 is in an actuated position. When the actuator 14 is in a non-actuated position, as shown in FIG. 11, there is a distance 48, preferably less than about two inches, between a top surface 50 of the actuator 14 and a bottom surface 52 of elongate body 12.

FIG. 8 shows a top view of the actuator 14 of FIG. 1. Referring to both FIG. 1 and FIG. 8 it can be appreciated that the actuator 14 has an opening 36 adapted to receive the lip 102 of the canister 100 and a detent 38 for forming a removable connection between the lip 102 of the canister 100 and the actuator 14. The actuator opening 36 is located substantially directly above the socket 20 of the elongate body 12. The detent 38 may be, for example, a clip, or an elastically deforming tab. The actuator 14 may also have a set of finger grips 46, as shown in FIG. 8, comprising at least an index finger grip to facilitate actuation of the medication. The elongate body 12 may also have a thumb depression 58 to complement the finger grips 46 and to assist in grasping, manuevering, holding or using the inhaler 10.

Figure 9:
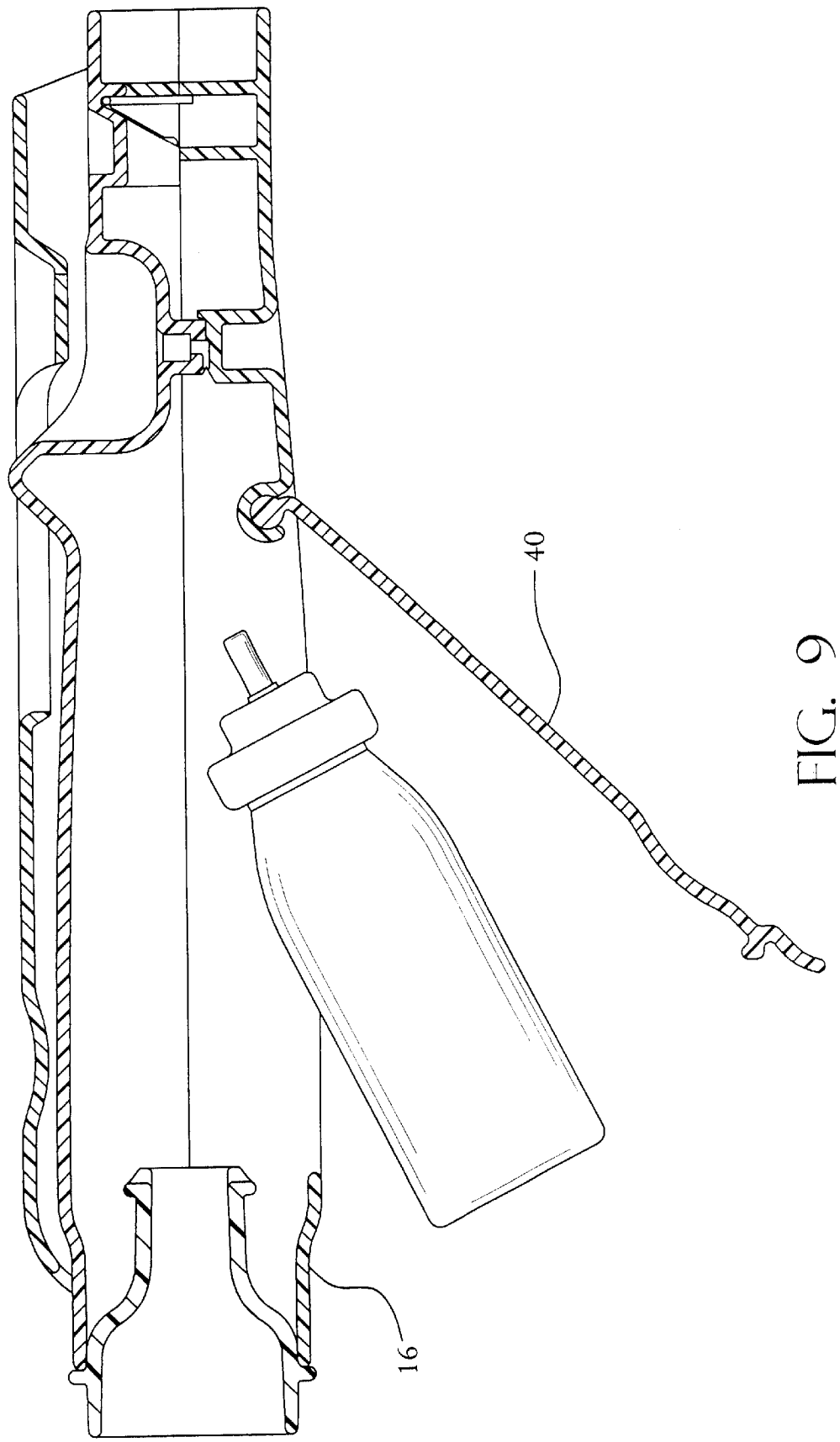
FIG. 9 shows an embodiment of the invention wherein the chamber comprises a chamber door pivotable along the length of the chamber.
Figure 10:
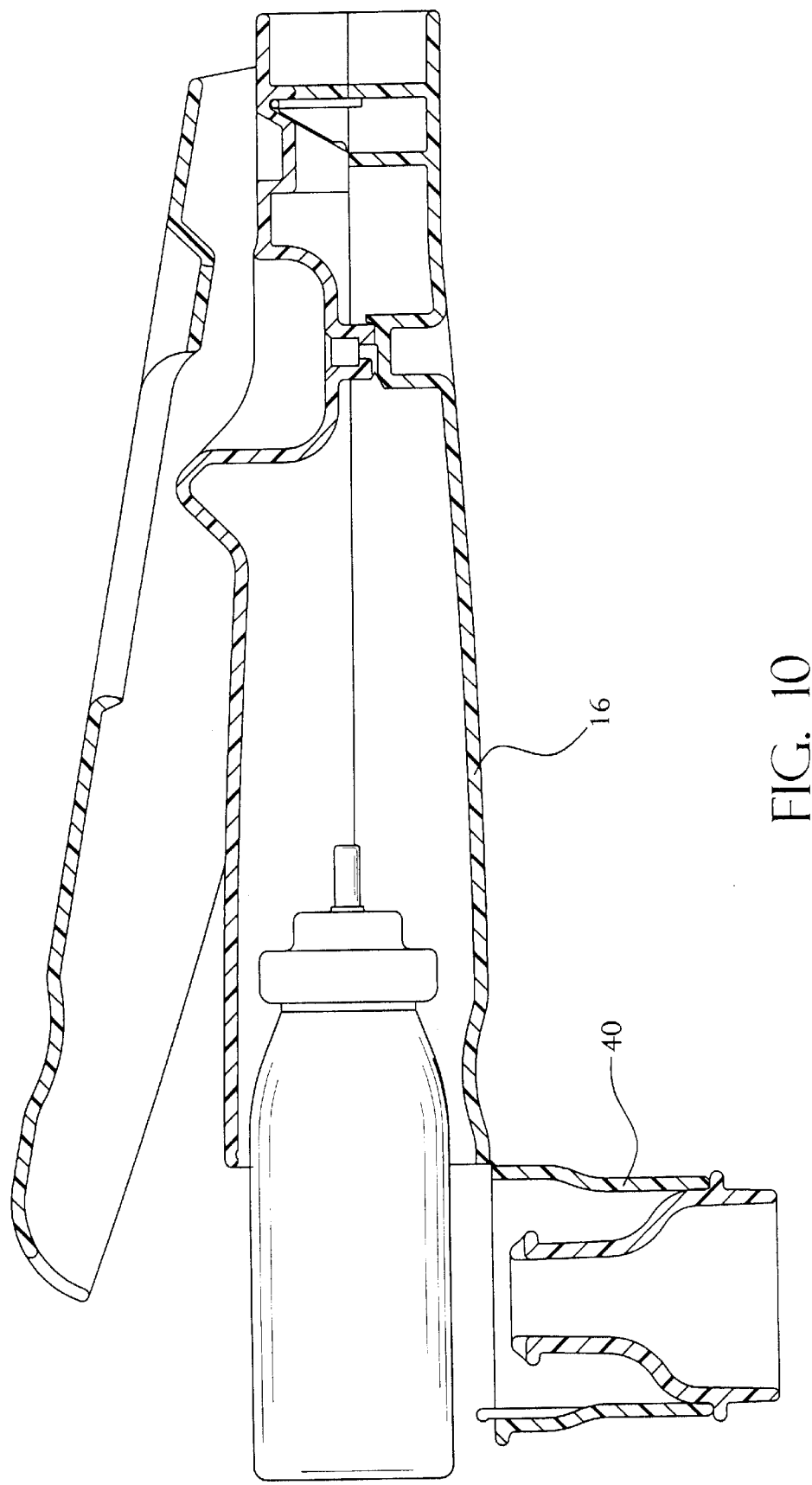
FIG. 10 shows an embodiment of the invention wherein the chamber comprises a chamber door pivotable perpendicular to the length of the chamber.

FIGS. 9 and 10 show embodiments of the invention wherein the inside of the chamber 16 is accessible via a pivotably attached chamber door 40. In the preferred embodiment illustrated in FIG. 9, a door hinge 42 connects the chamber door 40 to a chamber frame 44. Although FIG. 9 shows the chamber door 40 pivotable along the length of the chamber 16, the invention also contemplates a chamber door 40 pivotable perpendicular to the length of the chamber 16 as shown in FIG. 10.

Figure 13:
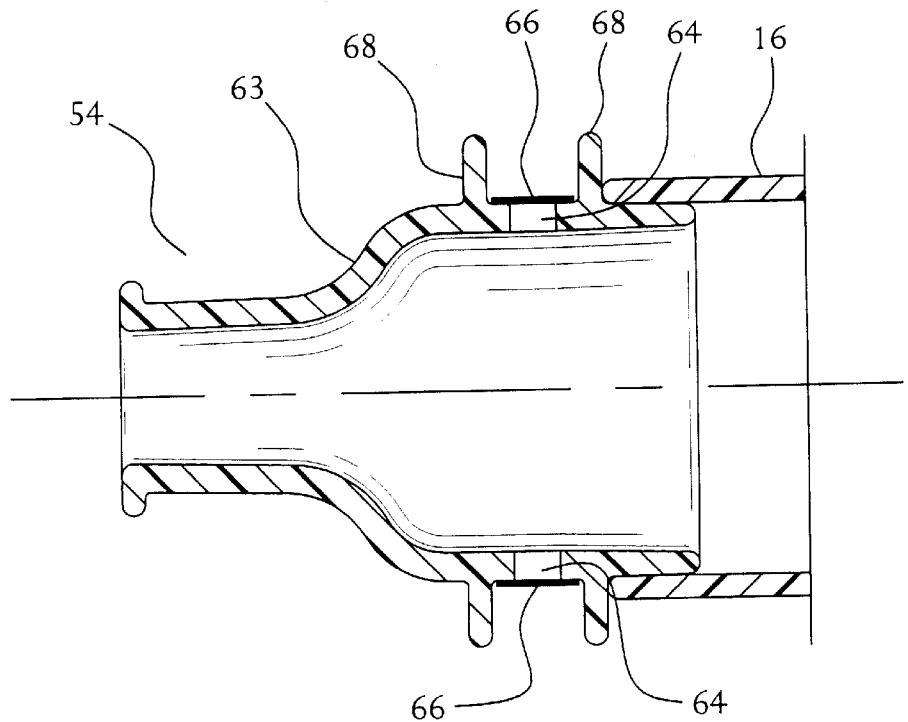
FIG. 13 shows a mouthpiece having a pair of flexible diaphragms, according to an embodiment of the invention. The diaphragms illustrated in FIG. 13 substantially seal a pair of fluid relief holes.
Figure 14:
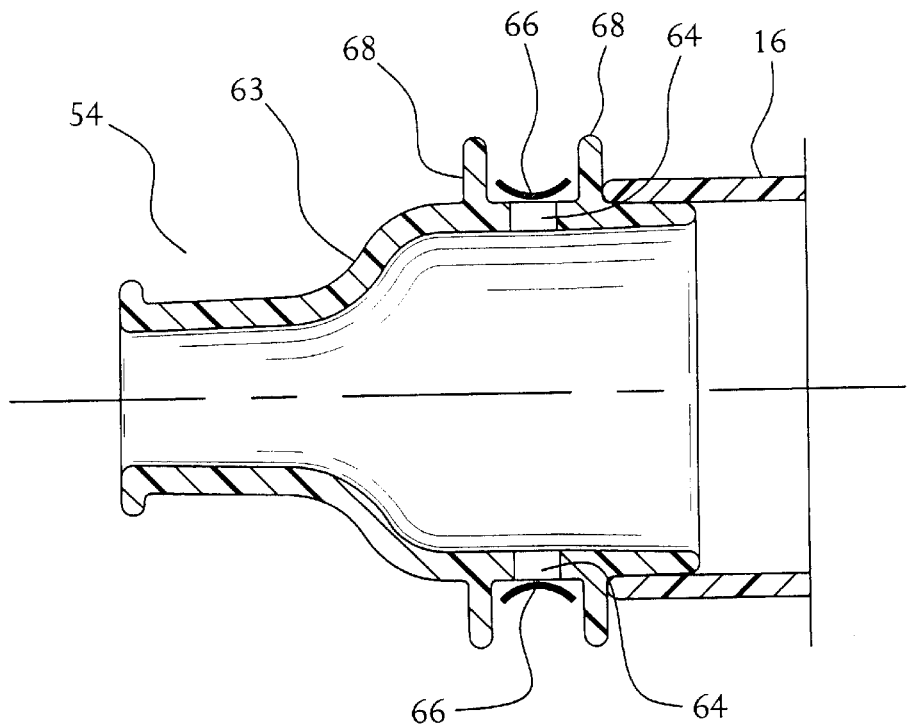
FIG. 14 shows the mouthpiece of FIG. 13 with the diaphragms substantially opened to provide open communication between the chamber and the ambient air.

FIGS. 13 and 14 show an embodiment of the invention wherein the mouthpiece 54 has a mouthpiece wall 63 forming a pair of fluid relief holes 64. The fluid relief holes 64 allow fluid to exit the mouthpiece 54 if the user exhales into the chamber 16. Preferably, as shown in FIG. 13, the mouthpiece 54 includes a pair of flexible diaphragms 66 adapted to substantially seal the fluid relief holes 64 when the user inhales through the mouthpiece 54. Upon exhalation by the user, the flexible diaphragms 66 are adapted to permit egress of fluid, as shown in FIG. 14. Optionally, the mouthpiece wall 63 has a pair of ridges 68 protruding therefrom adjacent to the flexible diaphragms 66. Although the embodiments shown in FIGS. 13 and 14 show a pair of fluid relief holes 64 and a pair of flexible diaphragms 66, the invention contemplates a single relief hole and diaphragm and multiple relief holes and diaphragms as well. Furthermore, it should be understood that each flexible diaphragm 66 should not be limited to the embodiment shown and is intended to include any pressure sensitive valve or member capable of responding to inhalation or exhalation through the mouthpiece 54.

The present invention may be embodied in other specific forms without departing from the spirit or essential attributes thereof and, accordingly, reference should be made to the appended claims, rather than to the foregoing specification, as indicating the scope of the invention.

What is claimed is:

1. An inhaler for releasing an aerosol from a container having a lip and an outlet normally sealed by a stem movable relative to the lip, the inhaler comprising:

an elongate body comprising a chamber having a first end and a second end, the chamber forming an opening at the first end of the chamber;

a stem block with a socket adapted to receive said stem of said container;

a dispensing nozzle adjacent to the stem block for providing communication between the socket and the chamber, the dispensing nozzle adapted to direct a discharge of said aerosol from said stem of said container into the chamber;

a flow restrictive valve in open communication with the chamber and responsive to a change in fluid pressure; and an actuator pivotably attached to the elongate body, the actuator having an opening adapted to receive said lip of said container and a detent for forming a removable connection between said lip of said container and the actuator, the actuator opening located substantially directly above the socket.

2. The inhaler of claim 1 wherein the chamber further comprises a first section adjacent to the first end and a second section pivotably attached to the first section.

3. The inhaler of claim 2 wherein the chamber is of sufficient volume and shape to store the container.

4. The inhaler of claim 1 wherein the dispensing nozzle is substantially located at the second end of the chamber.

5. The inhaler of claim 1 wherein the dispensing nozzle is further adapted to direct the discharge of said aerosol toward the opening of the chamber.

6. The inhaler of claim 1 wherein the chamber further comprises a chamber shape and wherein the dispensing nozzle has a valve shape selected according to the chamber shape.

7. The inhaler of claim 6 wherein the chamber is elliptically shaped and wherein the valve shape is tee-bar shaped, oval, conical or cylindrical.

8. The inhaler of claim 1 wherein the chamber is elliptically shaped.

9. The inhaler of claim 8 wherein the dispensing nozzle is further adapted to shape the discharge of said aerosol into a flattened plume.

10. The inhaler of claim 1 wherein the chamber has a volume in the range of about 120 cubic centimeters to about 150 cubic centimeters.

11. The inhaler of claim 1 wherein the chamber, the stem block and the dispensing nozzle are molded together as a unibody by a method of blow molding.

12. The inhaler of claim 1 wherein the predetermined maximum inhaled flow rate is in the range of about 1 to about 100 liters per minute.

13. The inhaler of claim 1 wherein the predetermined maximum inhaled flow rate is less than about 80 liters per minute.

14. The inhaler of claim 1 wherein the flow restrictive valve comprises a leaf valve moveable from a substantially open position to a substantially closed position at about a maximum predetermined maximum inhaled flow rate.

15. The inhaler of claim 14 wherein the flow restrictive valve further comprises a leaf valve stop to prohibit the leaf valve from closing at the predetermined maximum inhaled flow rate.

16. The inhaler of claim 1 wherein the flow restrictive valve comprises a flexible member moveable from a substantially open position to a substantially closed position at about a maximum predetermined inhaled flow rate.

17. The inhaler of claim 1 wherein the chamber opening is adapted to receive a mouthpiece.

18. The inhaler of claim 17 wherein the mouthpiece comprises a mouthpiece wall forming at least one fluid relief hole.

19. The inhaler of claim 18 wherein the mouthpiece further comprises a pressure sensitive valve adapted to substantially seal the at least one fluid relief hole when a user inhales through the mouthpiece, and adapted to permit fluid egress through the hole upon exhalation by the user.

20. The inhaler of claim 19 wherein the pressure sensitive valve is a flexible diaphragm.

21. The inhaler of claim 19 wherein the mouthpiece further comprises a ridge protruding from the mouthpiece wall substantially adjacent to the pressure sensitive valve.

22. The inhaler of claim 1 wherein the chamber opening is adapted to receive a mask attachment.

23. The inhaler of claim 1 further comprising a mouthpiece removably connected to the opening of the chamber.

24. The inhaler of claim 1 wherein the actuator is substantially parallel to the elongate body in an actuated position.

25. The inhaler of claim 1 wherein the actuator further comprises a top surface having an index finger grip and wherein the elongate body further comprises a bottom surface having a thumb depression.

26. The inhaler of claim 1 wherein the container is a pressurized canister.

27. The inhaler of claim 1 wherein the actuator further comprises a top surface the elongate body further comprises a bottom surface, and the bottom surface of the actuator and the top surface of the elongate body separated at the first end of the chamber by a distance of less than about two inches when the inhaler is in a non-actuated position.

* * * * *